May 7, 1940. M. H. HORVATH Plant Pat. 386
ROSE
Filed Dec. 7, 1939
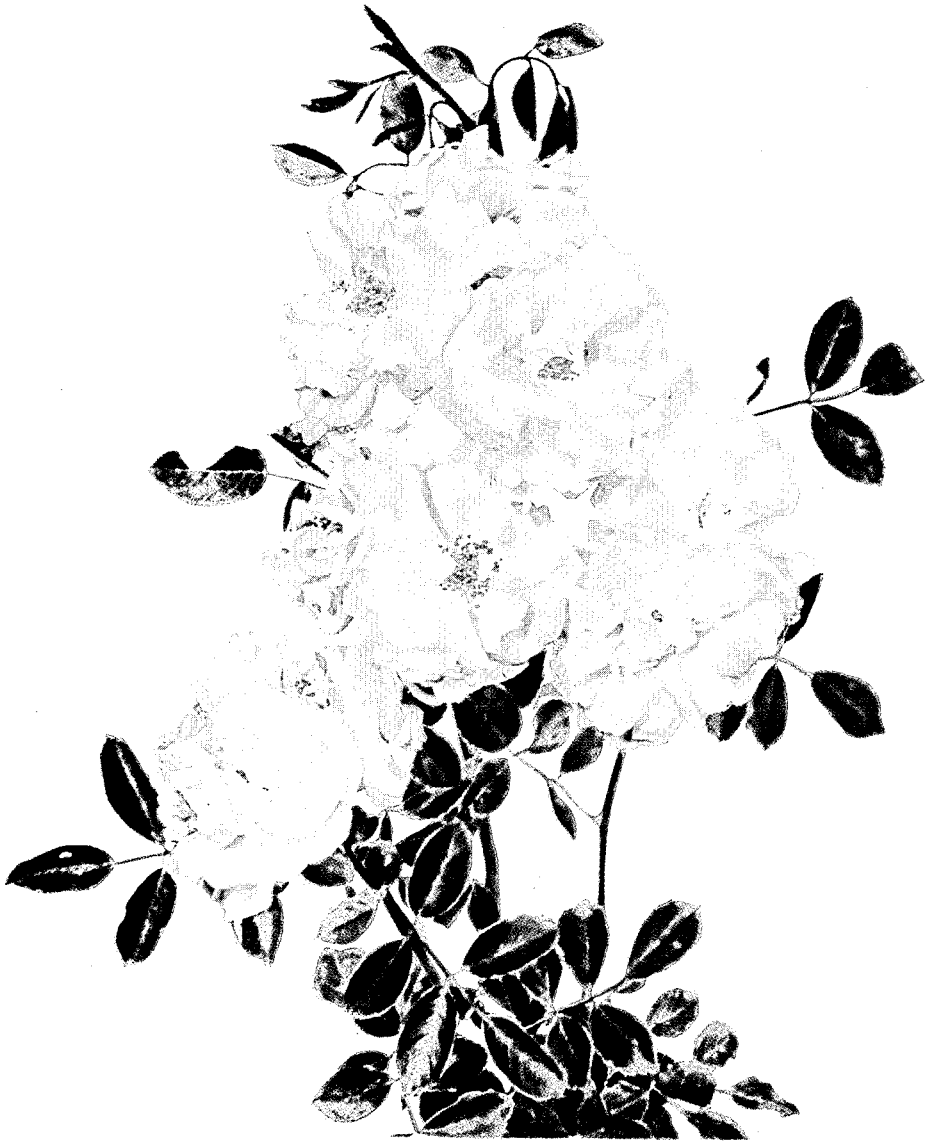
INVENTOR
MICHAEL H. HORVATH
BY John H. Rowand, Jr.
HIS ATTORNEY Patented May 7, 1940

Plant Pat. 386

UNITED STATES PATENT OFFICE

386

ROSE

Michael H. Horvath, Mentor, Ohio

Application December 7, 1939, Serial No. 308,039

1 Claim. (Cl. 47—61)

This invention relates to a new variety of rose, a *wichuraiana* hybrid.

The variety was originally produced by crossing a variety *wichuraiana*, as the female or seed parent, with a hybrid, as the male or pollen parent, which was produced by crossing a variety *"multiflora"* as the female parent and the variety *"Rosa foetida bicolor"* as the male, or pollen, parent. It has been asexually reproduced true to form in considerable quantity.

The variety is extremely hardy and above average in disease resistance. It has been grown unprotected in the northern regions of the United States and appears to be hardy and adapted for growth, unprotected, throughout the United States generally and elsewhere throughout regions in the temperate zones. It can be grown protected in colder regions.

The plant is a strong climber attaining a height of fifteen feet or more.

The leaves are smooth, small in size, medium in quantity, and light green in color, comparable to Maerz & Paul Plate No. 22–L–9, and are almost totally hidden by the blooms during the blooming season. The leaves are resistant to mildew and black-spot.

The plant produces a superabundance of pure white flowers, which are saucer-shaped. They are borne in umbells and threes, often semi-pendant on slender, limber stems, beginning generally at one and one-half to two feet from the base of the plant. They are massed in great abundance and profusion upwardly therefrom over the entire plant. The peduncles are from eight to eighteen inches long, slender and limber, and well proportioned to the number of flowers so that they support the flowers semi-pendantly.

The color of the flowers is pure white, comparable to Maerz & Paul Plate No. 1–A–1 throughout the entire blooming period. In all stages of blooming, the flowers have a glossy appearance or sheen, with golden centers, comparable to Maerz & Paul Plate No. 11–L–9.

Each flower has from twenty-five to thirty shell-shaped petals with slightly irregular cristate edges, and are irregularly imbricated.

The variety is characteristically a persistent grower and a profuse and abundant bloomer, rarely recurrent, the flowers being abundant throughout the blooming period which begins in June (northern Ohio) and lasts five to six weeks. During the blooming period the flowers are substantially consistent in quantity and quality.

The blooms and plant are excellent for cutting and the flowers have good lasting qualities both as to physical condition and color, whether cut or uncut.

The plant is distinguished principally by a most exceptional prolificacy of bloom, which so completely covers the growth that the plant resembles a single large and compact bouquet of glossy white blossoms. Additionally, it is distinguished by the purity and permanence of the white petals of the flowers, the very pronounced strong briar scent, and the hardiness of the plant and its resistance to black-spot and mildew.

The following tabulation is a detailed description of the new variety "Polaris."

*General*

Parentage:

*Seedling—seed parent.—Wichuraiana.*

*Pollen parent.*—A hybrid produced by crossing the species *"multiflora"* as the seed parent with the variety *"Rosa foetida bicolor,"* as the pollen parent.

Classification:

*Botanic.—Wichuraiana* hybrid.

*Flower*

Blooming habit:

Location where observations were made—trial field of Michael H. Horvath, Mentor, Ohio.

*Flowering.*—Rarely recurrent—blooms extremely abundant and constant through season.

Bud:

Size.—Small.

Form.—Semi-spherical, ovoid.

Color.—When sepals first divide—sulphur yellow. When petals begin to unfurl—lighter. When half blown—full white.

*Sepals.*—Small, regular, smooth, rounded, light green.

*Calyx.*—Shape—regular or normal. Size—medium. Aspect—somewhat covered with small needlets. Odor when rubbed—heavy tea-like.

*Peduncle.*—Length—eight to eighteen inches. Aspect—slender and smooth. Color—green with a reddish shade. Strength—limber. Opening—regular and constant through season.

Bloom:

*Size.*—Two to two and one-half inches.

*Borne.*—In large umbells and in threes, often semi-pendant, beginning eighteen inches from ground and completely covering growth so as to resemble a single large glossy white bouquet of roses.

*Stems.*—Slender.
*Form.*—When first opened—saucer-shaped.
*Permanence.*—Good.

Petalage: Number of petals under normal conditions, twenty-five to thirty.
*Color.*—Center of flower—pure white. Outer petals—pure white. Base of petals—pure white. Inside of petals—pure white. Reverse of petals—pure white. General tonality from a distance—pure white.
*Variegations.*—None.
*Discoloration.*—General tonality at end of first and second days—pure white. Third day—pure white until petals drop.

Petals:
*Texture.*—Light.
*Appearance.*—Inside—pure white, comparable to Maerz & Paul Plate No. 1–A-1. Outside—pure white.
*Form.*—Shell-shape with slightly irregular cristate edges.
*Arrangements.*—Irregularly imbricated.
*Petaloids in center.*—Up to one-half dozen.
*Persistence.*—Normal.
*Fragrance.*—Briar scent.
*Nature.*—Strong.
*Lasting quality.*—On plant—good. As a cut flower—good.

Genital organs:
*Stamens.*—Normal
*Color.*—Normal.
*Arrangement.*—Somewhat irregular.
*Stamens, filaments, (threads).*—Dull white.
*Pollen.*—Golden.
*Styles.*—Light green, medium and normal in size and normal arrangement.
*Stigmas.*—Whitish yellow, small and depressed.
*Ovaries.*—Sparse.

Fruit:
*Variety.*—Small.
*Form.*—Spherical and depressed.
*Aspect.*—Smooth.
*Color at maturity.*—Yellow
*Sepals.*—Regular and smooth.

*Plant*

Form: A climber, rather with short distances between nodes.
Growth: Vigorous and strong to fifteen feet or more.

Foliage: Glossy light green.
*Size.*—Small.
*Quantity.*—Medium.
*Color.*—New foliage: upper side—light green; under side—light green. Old foliage: upper side—light green comparable to Maerz & Paul Plate No. 22–L–9; under side—light green.
*Shape.*—Somewhat elongated at both tips, extremity curved and pointed, varying from linear to obovate.
*Texture.* — Upper side—smooth. Under side—smooth, glabrous. Ribs and veins—indistinct.
*Edge.*—Semi-serrated, serrations irregular.
*Rachis.*—Smooth, some prickles. Color—green with reddish shade, under side—green.
*Stipules.*—Indistinct.
*Disease resistance.*—Very resistant to rose diseases, black-spot and mildew.

Wood:
New Wood—Color—green with reddish shading. Bark—smooth and green.
Old wood—Color—green with reddish shading. Bark—smooth and green.

Thorns:
Quantity—On main stalks from base—sparse. On laterals from stalk—sparse.
Form—Curved downwardly and sharply pointed.
Position—Very irregular.
Prickles—None.
Short needles—None.

Having now fully shown and described my new variety of rose and the mode of its production, what I claim and desire to secure by Letters Patent of the United States is:

A rose variety as herein shown and described and characterized principally by its exceptional prolificacy of blooms of large compact clusters of flowers of pure glossy white and which completely cover the entire growth so as to resemble a single large and compact bouquet of glossy white blossoms, and further characterized by a pronounced briar scent, shell shaped petals with slightly irregular cristate edges; consistency of blooming throughout the blooming period, the purity and permanence of the white petals in cut and uncut condition, and by the hardiness and resistance to disease.

MICHAEL H. HORVATH.

CERTIFICATE OF CORRECTION.

Plant Patent No. 386. May 7, 1940.

MICHAEL H. HORVATH.

It is hereby certified that error appears in the printed specification of the above numbered patent requiring correction as follows: Page 2, first column, line 49, after "rather" insert --compact--; and second column, after "pointed," in line 31, and before "Position - Very irregular." in line 32, insert the following line -

-- Color - Brownish gray. --;

and that the said Letters Patent should be read with this correction therein that the same may conform to the record of the case in the Patent Office.

Signed and sealed this 18th day of June, A. D. 1940.

Henry Van Arsdale,
Acting Commissioner of Patents.

(Seal)